US006056970A

United States Patent [19]
Greenawalt et al.

[11] Patent Number: 6,056,970
[45] Date of Patent: May 2, 2000

[54] COMPOSITIONS COMPRISING HEMOSTATIC COMPOUNDS AND BIOABSORBABLE POLYMERS

[75] Inventors: Keith E. Greenawalt, Milton; Julia B. Gershkovich, Lexington, both of Mass.

[73] Assignee: Genzyme Corporation, Cambridge, Mass.

[21] Appl. No.: 09/074,146

[22] Filed: May 7, 1998

[51] Int. Cl.[7] ............................ A61F 13/00; A61K 38/36

[52] U.S. Cl. .......................... 424/426; 424/422; 424/423; 424/488; 424/495; 424/496; 424/497; 530/382; 530/381

[58] Field of Search .................................... 424/422, 423, 424/426, 488, 495, 496, 497; 530/380, 382, 384

[56] References Cited

U.S. PATENT DOCUMENTS

| | | | |
|---|---|---|---|
| 4,442,655 | 4/1984 | Stroetmann | 53/428 |
| 4,655,211 | 4/1987 | Sakamoto et al. | 128/156 |
| 4,810,775 | 3/1989 | Bendix et al. | 528/480 |
| 5,631,011 | 5/1997 | Wadstrom | 424/400 |
| 5,643,596 | 7/1997 | Pruss et al. | 424/426 |

*Primary Examiner*—Thurman K. Page
*Assistant Examiner*—Lakshmi Channavajjala
*Attorney, Agent, or Firm*—Wolf, Greenfield & Sacks PC

[57] ABSTRACT

Solid, fibrous bioabsorbable hemostatic compositions containing a bioabsorbable polymer and a hemostatic compound, methods for making the hemostatic compositions, and methods for using the hemostatic compositions are disclosed.

42 Claims, No Drawings

COMPOSITIONS COMPRISING HEMOSTATIC COMPOUNDS AND BIOABSORBABLE POLYMERS

BACKGROUND OF THE INVENTION

This invention relates to hemostatic compositions useful in the stemming or prevention of blood loss from surgical or traumatic wounds.

A hemorrhage of a blood vessel, body tissue, organ or bone can result in blood loss leading to hypovolemic shock and death. However, despite continued advances in trauma care, a significant number of trauma victims suffer fatal or severe hemorrhage every year. Many of these fatalities could be prevented if adequate means existed for on site control of blood loss. Hemophiliacs and patients receiving anticoagulant medication (e.g., during and/or after heart surgery) are also at high risk for rapid blood loss.

The use of fibrin as a coagulating substance for stopping bleeding and for sealing wounds has been widely accepted. Generally, such biological adhesives or "fibrin glues" are based on a two component system of fibrinogen and thrombin which when mixed form a fibrin coagulum by the cleavage of fibrinogen through the action of thrombin to form fibrin monomers that spontaneously polymerize to form a three dimensional network of fibrin. For example, Tisseel™ is a two-component kit containing a fluid thrombin component including calcium chloride and a somewhat more viscous fibrinogen component including factor XIII, fibronectin, aprotinin and plasminogen. The two components are delivered deep frozen in two separate syringes, or as two lyophilized powders with corresponding aprotinin and calcium solutions as solvents. Using this method, the fibrin glue consolidates when the two components are combined due to fibrin monomer aggregation. The setting rate is dependent on the thrombin concentration and varies from a few seconds (high thrombin concentration) to a couple of minutes (low thrombin concentration).

The major disadvantage of these preparations is that the water-like fluidity of the components renders them difficult to handle and administer. Although various efforts have been made to facilitate the administration of these compositions, for example, by the development of double-syringe applicators as described in U.S. Pat. No. 4,359,049, or a spray system as described in U.S. Pat. No. 4,427,651, the basic problem of low viscosity remains.

Wadstrom, U.S. Pat. No. 5,631,011 describes a method of increasing the viscosity of fibrin glue compositions by adding a biocompatible polymer capable of forming a viscous aqueous solution. The components of this system are provided in deep freeze solutions or as lyophilized powders which are diluted prior to use with aqueous solutions. The primary route of administration taught by Wadstrom is by a two component preparation. Thus, while Wadstrom emphasizes the advantages of increasing the viscosity of the solution over prior "water-like" fibrin glues, the components of this system still require additional preparation at the time of use. Wadstrom further teaches that compositions having a high viscosity are to be avoided because fibrin polymerization and adhesion to the tissues would be inhibited.

One currently used alternative to fibrin glue, is a biodegradable collagen patch ("TAF" patch). For example, Zimmerman and Schiele, U.S. Pat. No. 4,453,939, describe collagen carriers in the form of a foam, web or film that is coated with a mixture of blood-clotting components including fibrinogen and thrombin. To prevent reaction of the blood-clotting components prior to use, they are provided as a suspension in an organic solvent which is applied to the collagen by brushing, spraying or dipping. However, difficulties in achieving optimum timing for the fixing procedure have been reported using this method resulting in inconsistent attachment and stability of the active components onto the collagen carrier. Moreover, penetration of the active components beyond the surface of the collagen carrier is not possible using this method, thereby limiting the concentration of blood-clotting components available to the surface of the device. Another problem with the TAF patches is that the collagen fleece/foam used does not provide sufficient mechanical support once wet, preventing application of manual pressure to assist in stopping blood flow or repositioning of the patch once it has been applied to the wound. Further, surgeons have reported that the inflexibility of the TAF patch prevents them from easily conforming to the contours of the site to which they are applied. Still another problem with TAF patches is that they require refrigeration prohibiting use outside a clinic or hospital setting.

WO 96/17633 describes tissue sealants including a fibrin bandage. In the method used for generating the bandage, the active components are lyophilized in separate layers which are supported by an occlusive backing. Therefore, the active components are not homogeneously mixed throughout the bandage.

Accordingly, there is a need for hemostatic compositions that are sturdy enough to withstand manual pressure and which are less complicated to use, especially in emergency situations such as life-threatening traumas wherein stemming blood flow as fast as possible can be critical.

SUMMARY OF THE INVENTION

In one aspect, the invention features a hemostatic, biocompatible composition in the form of a fibrous solid that is bioabsorbable. The composition contains a bioabsorbable polymer and one or more hemostatic compounds. Preferably, the hemostatic compound is thrombin, more preferably, the composition contains thrombin and a calcium salt, and most preferably also includes fibrinogen. A "hemostatic compound or composition," as used herein, is a substance or composition that, upon application to a wound reduces or stops blood loss by promoting blood clot formation. By the term "fibrous" as used herein is meant a composition comprising natural or synthetic fibers. By "fiber" is meant a unit of matter, either natural or manufactured, that forms the basic element of fabrics and other textile structures. A fiber is characterized by having a length at least 100 times its diameter or width.

The bioabsorbable polymers contained within the hemostatic composition of the invention include polyanionic polysaccharides, alginic acid, chitin, chitosan, fibrin, polyglycolide, polylactide, polycaprolactone, dextran and copolymers thereof. The term "polymer," as used herein refers to a molecule made by the repetitive bonding of at least two, and preferably more than two, repeating monomeric smaller units (e.g., monosaccharide, amino acid, nucleotide, alkene, or organic acid units). Accordingly, the term copolymer refers to a polymer formed by combination of two or more copolymerized monomeric or polymeric species. The term "bioabsorbable," as used herein, refers to the ability of a tissue-compatible material to degrade in the body after implantation into nontoxic products which are eliminated from the body or metabolized (Barrows, "Synthetic Bioabsorbable Polymers," p. 243, In: *High Performance Biomaterials—A comprehensive Guide to Medical and Pharmaceutical Applications*, Michael Szycher, ed., Technomic Publishing, Lancaster, Pa., 1991). Generally, the concentration of bioabsorbable polymer used in the hemostatic compositions of the invention is in the range of 0.1 to 50 mg/cm$^2$; preferably the concentration of bioabsorbable polymer is in the range of 0.1 to 30 mg/cm$^2$; and more preferably the concentration of the bioabsorbable polymer ranges from 0.1 to 10 mg/cm$^2$.

In one preferred embodiment, the bioabsorbable polymer is a polyanionic polysaccharide. A "polyanionic polysaccharide" (PAS) as the term is used herein, is a polysaccharide, including non-modified as well as chemical derivatives thereof, that contains more than one negatively charged group (e.g., carboxyl groups at pH values above about 4.0) and includes salts thereof, such as sodium or potassium salts, and alkaline earth metal salts such a calcium or magnesium salts. Preferred polyanionic polysaccharides contained in the hemostatic composition of the invention include, but are not limited to, hyaluronic acid (HA), carboxymethylcellulose (CMC) carboxymethylamylose (CMA), chondroitin-6-sulfate, dermatin sulfate, dermatin-6sulfate and combinations thereof.

Most preferably, the polyanionic polysaccharide is HA, CMC or CMA which is in the form of a water-insoluble derivative. A "polyanionic polysaccharide derivative," as the term is used herein, is one or more polyanionic polysaccharides (PAS) that are chemically modified from the native form. Such modifications can include the addition of functional groups (e.g., substituted amide groups, ester linkages, and amine groups); reactions that increase the water insolubility of the PAS by covalently cross-linking the PAS molecules; and reactions that increase the water-insolubility of the PAS by noncovalent interactions. Additionally, the hemostatic composition can include two or more polyanionic polysaccharides or their water-insoluble derivatives, e.g. HA and CMC or HA and CMA.

In another preferred embodiment, the polyanionic polysaccharide is combined with one or more hydrophobic bioabsorbable polymers or copolymers. As used herein, "hydrophobic," refers to compounds or compositions which lack an affinity for water. Preferably, the hydrophobic bioabsorbable polymer is chosen from the group consisting of polyglycolide, polylactide (D, L or DL), polydioxanones, polyestercarbonates, polyhydroxyalkonates, polycaprolactone (polylactones), and copolymers thereof. More preferably, polyglycolide, polylactide, or copolymers of polyglycolide-caprolactone, polyglycolide-polylactide, or polylactide-polycaprolactone are used in the composition of the invention. The concentration of hydrophobic bioabsorbable polymer used in combination with the polyanionic polysaccharide is preferably in the range of 0.1 to 50 mg/cm$^2$.

The thrombin used in preferred embodiments of this aspect of the invention can be of animal or human origin. For example, thrombin obtained from one mammalian species (e.g., bovine, pig, sheep) can be incorporated into compositions of the invention used to treat another mammalian species, for example, humans. More preferably, the thrombin used in the composition is from the same species for which the composition is intended to be used. The term "thrombin" as used herein includes natural thrombin molecules derived from animal or human plasma, and synthetic forms such as those produced by recombinant DNA technology including functionally active analogs that effectively maintain clotting activity in an animal or human. Thrombin is present in the hemostatic composition of the invention in a concentration of 1 to 100 U/cm$^2$, and preferably between 10 to 50 U/cm$^2$. A unit of thrombin, as used herein, is defined as the amount of thrombin required to clot a standardized 1 ml fibrinogen (~250 mg/dl) solution in 15 seconds.

The concentration of calcium chloride used in preferred embodiments of this aspect of the invention is sufficient to allow for activation of the thrombin. Typically, the concentration of calcium will vary between 0.01 to 10 mg/cm$^2$. The particular concentration of calcium used will depend on the specific purpose of the composition and can be readily determined by the skilled artisan using the teachings herein.

In other preferred embodiments of this aspect of the invention, the hemostatic composition includes fibrinogen. The fibrinogen can be of animal or human origin, and is preferably from the same species for which the composition is intended to be used. By the term "fibrinogen," as used herein, is meant to include natural fibrinogen molecules derived from animal or human plasma, and synthetic forms such as those produced by recombinant DNA technology including functionally active analogs that effectively maintain clotting activity in an animal or human. The fibrinogen used in the compositions of the invention can be highly purified, can contain small amounts of clotting factor XIII, or can be enriched with clotting factor XIII. Typically, the amount of clottable fibrinogen is present in the hemostatic composition of the invention in a concentration between about 0.05 and 20 mg/cm$^2$, preferably between about 1 and 20 mg/cm$^2$, and more preferably between about 5 and 15 mg/cm$^2$.

Additional blood-clotting constituents and fibrinolysis inhibitors can also be included in the compositions of the invention. Examples include, but are not limited to, Factor XIII, fibronectin, plasminogen, aprotinin, alpha-2-antiplasmin, alpha-2 macroglobulin, alpha-1-antitrypsin, epsilon-aminocaproic acid or tranexamic acid, or a plasmin activator inhibitor, e.g., PAI-1 or PAI-2.

In a further embodiment, the hemostatic composition of the invention can also contain an amount of the agent protamine sulfate effective to neutralize heparin present in the local environment of the area of application. Protamine sulfate neutralizes heparin or vitamin K antagonists that are present in the blood of certain patients who, for example, are undergoing parental therapy with heparin.

The compositions of the invention can further include a drug. The particular drug used is a matter of choice depending on the intended use of the composition. Preferred drugs include, but are not limited to, growth factors, growth-factor inhibitors, antibodies, non-steroidal anti-inflammatory drugs, antibiotics, and cytostatics.

The hemostatic composition of the invention typically has a mass/area (M/A) between about 15 to 100 mg/cm$^2$, preferably a M/A between about 20 to 60 mg/cm$^2$, more preferably a M/A between about 30 to 40 mg/cm$^2$. The size and shape of the composition will vary depending on the particular use. For example, in certain preferred embodiments the hemostatic composition can be supplied in a variety of standard rectangular or circular sizes, such as those commonly used in first-aid kits, triage, and surgery, and which can be further cut and sized to the particular area being treated. Alternatively, the hemostatic composition can be provided in a variety of other shapes which are useful for packing into body cavities, including, but not limited to spherical, conical, cuboidal or cylindrical shapes.

In further related embodiments, the hemostatic composition is contained within a sealed, waterproof, sterile package which facilitates removal of the compositions without contamination. Preferred waterproof packaging materials include, for example, aluminum foil, plastic, or other conventional material that is easily sterilized. Sterilization can be accomplished, for example, by subjecting the packaged composition to radiation, for example, gamma radiation or E-beam, or by treatment with ethylene oxide.

In another aspect, the invention features a method of making a solid, fibrous, bioabsorbable hemostatic composition which includes the steps of combining a bioabsorbable polymer and one or more hemostatic compounds in the presence of a non-aqueous solvent and subjecting the combination to a paper-making process to produce a solid, bioabsorbable hemostatic composition.

In one preferred embodiment of this aspect of the invention, the method involves precipitating the components of the hemostatic composition either separately or together into a non-aqueous solvent, admixing the precipitated components under conditions sufficient to form a fibrous pulp, and then collecting, pressing and drying the fibrous pulp to produce a solid, bioabsorbable hemostatic composition.

Examples of organic solvents which can be used in the method of the invention include straight-chain or branched $C_1$–$C_5$-alcohols, especially n-propanol, isopropanol, n-butanol, isobutanol and ethanol; ketones, for example, acetone or methyl ethyl ketone; aliphatic or cycloaliphatic ethers, for example dimethyl ether or diethyl ether, tetrahydrofuran or dioxane; esters, for example, ethyl acetate; nitrites, for example, acetonitrile; and aliphatic halogenated hydrocarbons, for example, carbon tetrachloride, methylene chloride and chloroform.

In preferred embodiments of the method of the invention, admixing of the components occurs under high shear conditions to evenly disperse the materials in the organic solvent. One preferred method of collecting the fibrous pulp uses forming fabric. The term “forming fabric” refers to a material used during paper formation that permits the drainage of the pulp solution while retaining the fibers, provides mechanical support, imparts surface characteristics during pressing and drying, and is released from the dried paper product. The forming fabric can be a variety of materials including, but not limited to a Teflon or stainless steel mesh screen, and preferably is a polyester woven fabric. In other preferred embodiments, the fibrous pulp is collected onto the forming fabric under vacuum conditions; the wet pulp collected is subjected to heat compression; and air dried at room temperature, or preferably under heated conditions, for example, between 80 to 140° F., and most preferably is dried at 100 to 135° F.

In related embodiments of this aspect of the invention, the methods of the invention can produce a hemostatic composition in which the hemostatic compounds are evenly dispersed throughout the composition, or supplied as a gradient, for example, by collecting fibrous pulps containing a range of desired concentrations of the hemostatic compound or compounds one after the other prior to the steps of pressing and drying. Alternatively, the methods of the invention can be used to produce a multilayered hemostatic composition. For example, bilayer compositions containing one layer of bioabsorbable polymer and another layer containing one or more hemostatic compositions can be produced by collecting a fibrous pulp of the bioabsorbable polymer after collection of the fibrous pulp of the hemostatic compound and then combining the pulps in layers prior to the pressing and drying steps. Trilayer compositions can also be produced, for example, having hemostatic compounds on both sides of a core containing a bioabsorbable polymer.

In still another aspect, the invention includes a method of inhibiting or stopping blood loss from a wound by applying to the wound a solid hemostatic composition containing a bioabsorbable polymer and one or more hemostatic compounds. Preferably, the composition is maintained in contact with the wound preferably with light pressure (e.g., manual) for a period of time sufficient for blood clotting to occur at the interface between the composition and the wound and for bleeding to be substantially arrested. Generally, the hemostatic composition is maintained in contact with the wound surface for a period of about 20 seconds to 10 minutes, preferably about 20 seconds to 5 minutes, and more preferably about 20 seconds to 2 minutes. The composition can be applied directly to the wound alone, or can be held in place by means of a dry sterile material such as gauze. Depending on the location of the wound, a bandage, including an elasticized bandage can be wrapped around the patch so as to provide pressure to the wound site.

Preferred embodiments of this aspect of the invention include use of the hemostatic composition for topical treatment to inhibit or stop bleeding of wounds due to trauma or surgery. In additional preferred embodiments, the method of the invention uses the hemostatic composition to inhibit or stop bleeding of a parenchymal organ, such as the liver, kidney, spleen, pancreas or lungs. Alternatively, the methods include inhibiting or stopping bleeding or fluid loss during surgery including, but not limited to, abdominal, vascular, urological, gynecological, thyroidal, neurosurgery, tissue transplant, and dental surgery.

In further embodiments, the hemostatic composition can also be provided for use to anastomose or fuse ends of a blood vessel or other body lumen that has been severed, for example, during surgery. In this embodiment, the hemostatic composition is provided in a form that is easily fit to the ends of a vascular prosthesis. In cases where the vascular prosthesis is synthetic, such as a Dacron graft, the hemostatic composition can be provided in a form (e.g., cylindrical) sized to easily fit over the ends of the graft. Accordingly, also provided are kits that contain a vascular prosthesis and a hemostatic composition of the invention designed for fitting with the ends of the prosthesis. Alternatively, in cases wherein pre-sizing is not possible (e.g., natural grafts) the hemostatic composition can be provided in a form that is easily wrapped around the prosthesis just prior to use.

Additionally, a hemostatic composition according to the invention which is intended for topical applications can be applied with an adhesive tape, or adhered to an adhesive backing in a Band-Aid form. The type of adhesive used can be any type of medically acceptable adhesive. Preferably the adhesive used is porous to areas which contact the skin to allow diffusion of oxygen.

A kit is also provided which according to the invention comprises any of the above described embodiments of the hemostatic composition. For example, the kit can contain multiple hemostatic compositions, preferably wherein each is provided in a separate, waterproof, sterile package. Additionally, a kit designed for emergency or military use can also contain disposable pre-sterilized instruments, such as scissors, scalpel, clamp, tourniquet, elastic or inelastic bandages, or the like.

An important advantage of the hemostatic composition of the present invention is that the mechanical integrity of the composition is maintained after contact with body fluids allowing application of manual pressure to promote stoppage of blood flow, and repositioning of the composition when necessary. In further contrast to prior art compositions, the active components necessary to promote hemostasis are dispersed throughout the composition avoiding the problem of separation of different layers thereby allowing the compositions to be cut and sized to the particular wound being treated.

Accordingly, the hemostatic compositions of the invention provide a means for rapidly reducing bleeding in trauma victims and surgical patients without the time delay associated with solubilization and mixing of components. The hemostatic compositions can be readily used by untrained individuals as well as medical personnel. These characteristics allow use of these compositions in field applications, such as in trauma packs for soldiers, rescue workers, ambulance/paramedic teams, firemen, and by emergency room personnel, and in first aid kits for the general public use. Thus, utilization of the hemostatic compositions of the invention will result in a reduction of fatalities due to trauma and also decrease the demand upon the available blood supply during instances of severe natural or man-made disasters.

Unless defined otherwise, all technical and scientific terms used herein have the same meaning as commonly understood by one of ordinary skill in the art to which this invention pertains. Although any method and materials similar or equivalent to those described herein can be used in the practice or testing of the present invention, the preferred methods and materials are now described. All publications mentioned hereunder are incorporated by reference. Unless mentioned otherwise, the techniques employed or contemplated herein are standard methodologies well known to one skilled in the art. The materials, methods and examples are illustrative only and not intended to be limiting.

Other features and advantages of the invention will be apparent from the following description and from the claims.

DETAILED DESCRIPTION OF THE INVENTION

A process is described for producing a solid, fibrous hemostatic composition containing proteins including, but not limited to, thrombin, or a combination of thrombin and fibrinogen, and salts such as, but not limited to, calcium chloride in combination with one or more bioabsorbable polymers.

Materials

Fibrinogen and thrombin for use in the invention can be readily obtained from a number of commercial sources (e.g., Sigma, CalBiochem, American Diagnostics, Inc.). Alternatively, these proteins can be derived from the plasma of any desirable species, or produced using recombinant DNA methods (e.g., Prunkard et al., *Nature Biotechnology* 14:867–871, 1996; Velander, WO 95/22249; Karges and Metzner, *Seminars in Thrombosis and Hemostasis,* 22:427–436, 1996; Lewis et al., *Biochemistry* 36:995–1002, 1997; Lai et al, *J. Biol. Chem.* 269:24596–24601, 1994; Fischer et al., *Thrombosis Res.* 81:157–162, 1996; Lord et al., *Blood Coagulation and Fibrinolysis* 4:55–59, 1993; DiBella et al., *I Biol. Chem.* 270:163–169, 1995; Roy et al., *J. Biol. Chem.* 270:163–169, 1995).

Preferably, the fibrinogen and thrombin used are of bovine or human origin. When the composition is to be used in humans, the fibrinogen and thrombin are most preferably of human origin. Additionally, when the fibrinogen is derived from human plasma it is preferably subjected to heat inactivation methods, or even more preferably to solvent detergent methods, well known to those skilled in the art and intended to inactivate any viruses that might be present (e.g., see Radosevich et al., "Fibrin Sealant: Scientific rationale, production methods, properties, and current clinical use," *Vox Sang* 72:133–143, 1997).

Bioabsorbable biopolymers for use in the composition of the invention can be obtained from a variety of standard commercial sources (e.g., Genzyme Corp., Aqualon, Birmingham Polymers, Deknatel). Water-insoluble polyanionic polysaccharide compositions can be prepared by a number of methods for use in this invention. For example, derivatives can be generated via the formation of covalent intra- and inter-chain crosslinks as previously described (e.g., see Sparer et al., 1983, Chapter 6, pages 107–119, in Roseman et al., *Controlled Release Delivery Systems*, Marcel Dekker, Inc., New York; DeBelder et al., PCT Publication No. WO 86/00912; Balazs et al., 1986 U.S. Pat. No. 4,582,865; Malson et al., 1986, PCT Publication No. WO/86/00079; and Prestwich et al., EP Publication No. 0416250A2, 1991). Water insoluble compositions which do not contain covalent cross-links between polyanionic polysaccharide molecules and compositions containing polyanionic polysaccharides can be formed using the methods described in Hamilton et al., U.S. Pat. No. 4,937,270, Burns et al., U.S. Pat. No. 5,017,229, U.S. Ser. No. 07/703,254, 07/833,973, and compositions containing combinations of polyanionic polysaccharides and hydrophobic polymers or copolymers are described in U.S. Ser. No. 08/318,987 (all of the above hereby incorporated by reference).

Preparation of Hemostatic Compositions

Generally, compositions according to the invention are formed by precipitating thrombin (with or without biopolymers and calcium chloride) by injecting the aqueous solution using a syringe into a rapidly stirring non-aqueous solvent coagulation bath containing ethanol, isopropanol, butanol or a combination thereof. In compositions containing a combination of thrombin and fibrinogen, a second aqueous solution containing fibrinogen (with or without biopolymers and calcium chloride) is also precipitated into fibers using a non-aqueous solvent in the same manner. The fibrous precipitate(s) is then washed with the non-aqueous solvent to purify and dewater.

The desired fibrous precipitate or combination of precipitates (e.g., thrombin and biopolymer; thrombin, fibrinogen and biopolymer; thrombin/biopolymer; thrombin/biopolymer and fibrinogen; thrombin and fibrinogen/biopolymer; and thrombin/biopolymer and fibrinogen/biopolymer) are high shear mixed to form a fibrous pulp solution in the non-aqueous solvent. The pulp solution is then collected, pressed and dried using existing paper-making technology, (see, e.g., *Handbook for Pulp & Paper Technologists*, Smook, G. 2nd edition, Angus Wilde Publications Inc., 1994), and as described in the following examples. The resulting paper-like structure consists of dry thrombin, or thrombin and fibrinogen in combination with one or more biopolymers, and can additionally contain calcium and/or other agents as described herein. Since all of the precipitation, mixing and paper-making steps are in a non-aqueous solvent and not in water, the thrombin does not activate fibrinogen during processing. The resulting, solid, fibrous, dried composition can contain the hemostatic components distributed throughout the paper-like material. Alternatively, a paper-like composition can be generated which has a concentration gradient of the desirable hemostatic components, for example, by collecting fibrous pulps containing varying concentrations of the hemostatic components prior to compression and drying. Upon activation by blood, body fluids, saline or water, the composition acts as a hemostatic patch.

In another variation of the invention, the proteins and salts can be added to a non-aqueous slurry containing the biopolymer. For example, commercially available lyophilized fibrinogen, thrombin and calcium chloride powders can be added to the bioabsorbable polymer (e.g., HA/CMC and/or PGA) fibers in ethanol. The mixture can then be collected, pressed and dried according to existing papermaking technology to form a paper-like structure with hemostatic components homogeneously dispersed throughout the thickness. This paper-like structure has superior mechanical properties compared to prior art materials. Moreover, since all of the precipitation, mixing and papermaking steps are in a non-solvent and not in water, the thrombin does not activate fibrinogen during processing.

Bilayer compositions can also be made with one side containing the hemostatic agents and the other side being non-hemostatic and non-adhesiogenic. For example, the hemostatic side can contain fibrinogen, thrombin and calcium chloride and the non-adhesiogenic side can contain HA/CMC. Alternatively, the hemostatic side can further contain one or more bioabsorbable polymers as described herein, whereas the non-adhesiogenic side would contain a bioabsorbable polymer without the hemostatic components. HA/CMC has been demonstrated to reduce post-surgical adhesion formation (e.g., Becker et aL, *British J. Surg.* 82:Suppl 1, 1995). Therefore, the side containing the hemostatic components will provide hemostasis, while the side containing the bioabsorbable polymer, e.g., HA/CMC, would prevent adhesions. Each side of the bilayer composition can be marked for appropriate placement, e.g., by the addition of a biocompatible dye such as riboflavin to one of the bilayers.

The paper-like compositions generated according to the herein described methods can also be used alone or in combination with tri-layer laminated technology such as that described in U.S. Ser. No. 08/318,987. Tri-layer composites can be made by laminating the hemostatic paper-like membrane to a hydrophobic bioabsorbable polymer core, such as polyglycolide, polylactide, polycaprolactone, or copolymers thereof. The tri-layer composition can have hemostatic components laminated on both sides of the core which would provide hemostatic activity to both surfaces while increasing the strength and in vivo residence time of the device with the addition of the core polymer. Alternatively, the hemostatic components can be laminated to one side of the core while laminating a nonadhesiogenic material such as HA/CMC to the other side thereby producing a device with one hemostatic surface and one non-adhesiogenic surface.

Additional Components

In addition to the hemostatic agents, the compositions of the invention can further contain components which promote wound healing and prevent infection such as, but not limited to polypeptide growth factors, non-steroidal anti-inflammatory agents, antibiotics, and cytostatics. The concentration(s) of the additional components will vary depending on the desired objective, and should be sufficient to accomplish the particular purpose for which they are used. The amount of each component can be readily determined by those skilled in the art, for example, by empirically testing various concentrations and selecting that which is effective for the intended purpose and the site of application.

Examples of polypeptide growth factors which are known to play a role in healing include, but are not limited to: platelet-derived growth factors (PDGFs); insulin-binding growth factor-1 (IGF-1); insulin-binding growth factor-2 (IGF-2); epidermal growth factor (EGF); transforming growth factor-$\alpha$ (TGF-$\alpha$), transforming growth factor-$\gamma$ (TGF-$\gamma$); platelet factor 4 (PF-4); fibroblast growth factor (FGF); and heparin binding growth factors one and two (HBGF-I and HBGF-2). The growth factor, or mixture thereof, can be prepared by any method known to those skilled in the art, or can be purchased from a variety of commercial sources. The selection of the particular growth factor(s) used will depend on the desired application and can be readily determined by those skilled in the art.

The invention is described in more detail in the following examples. These examples are given by way of illustration and are not intended to limit the invention except for as set forth in the claims.

EXAMPLE 1

Thirty-seven milliliters of an aqueous fibrinogen solution (40 mg/ml) was injected using a syringe into approximately 700 ml of 95% ethanol while stirring. The fibrous precipitate that resulted was stored in ethanol overnight. A portion of the ethanol was decanted and all of the fibrinogen precipitate (1.48 g) in 540 ml of 95% ethanol was high shear mixed at 4000 rpm for 30 seconds with a Ultra-Turrax T50 homogenizer. The resulting pulp solution was stored in 95% ethanol.

Forty milliliters of fibrinogen pulp solution was diluted with 200 ml of 95% ethanol. To this furnish solution was added 20 mg of thrombin powder and 80 mg calcium chloride. The sample was collected on forming fabric using a Millipore filter housing (dia.=7.4 cm). The wet sample was pressed at 2 metric ton for 15 seconds and air dried to produce an extremely thin membrane.

EXAMPLE 2

One-hundred-twenty milliliters of fibrinogen pulp solution prepared as described in Example 1 was diluted with 200 ml of 95% ethanol. To this furnish solution was added 40 mg of thrombin powder, 160 mg calcium chloride and 20 ml of modified hyaluronic acid/carboxymethyl cellulose pulp solution obtained by precipitating carbodiimide modified HA/CMC (modified as described in U.S. Pat. No. 5,017,229) into ethanol, and high shearing the resulting fibrous precipitate into a pulp-like ethanol slurry. The mixture was collected as described for Example 1 on standard forming fabric using a Millipore filter under vacuum assist, pressed at 2 metric ton for 15 seconds, and air dried. A paper-like membrane resulted.

EXAMPLE 3

Three milliliters of an aqueous fibrinogen solution (40 mg/ml) was injected with a syringe into ~100 ml of 100% ethanol while stirring. The fibrous precipitate that resulted was collected on a polyester filter. A small sample of the dry material (~1 $cm^2$) was placed in 30 ml of deionized water with 5 mg of thrombin and 100 mg of calcium chloride. The material formed a fibrin clot immediately.

EXAMPLE 4

0.22 g of lyophilized fibrinogen powder was added to 65 ml of HA/CMC pulp (0.22 g HA/CMC in 100% ethanol). Also added to this mixture was 28 mg of calcium chloride powder and 3.3 mg of thrombin powder. The mixture was diluted with and additional 340 ml of 100% ethanol and high shear blended with an Ultra-Turrax T50 with a G45F dispersing head for 45 seconds at 5,000 rpm. The mixture was then collected on forming fabric using a Millipore filter housing (dia.=7.4 cm). The wet sample pressed twice at 10 psi with a roll press and air dried. A paper-like membrane resulted similar to that produced in Example 8 discussed below.

EXAMPLE 5

Sixty-five milliliters of HA/CMC pulp (0.22 g HA/CMC in 100% ethanol) was diluted with 340 ml of 100% ethanol and collected on forming fabric using a Millipore filter housing (dia.=7.4 cm). Then a solution containing 65 ml of HA/CMC pulp, 0.22 g of lyophilized fibrinogen powder, 29 mg of calcium chloride and 3.8 mg of thrombin was diluted with 340 ml of 100% ethanol and collected on top of the HAICMC wet cake. The wet sample was pressed two times at 10 psi with a roll press and dried at 100° F. with a drum dryer. A thick bi-layer paper-like membrane resulted that was enriched with active fibrinogen/thrombin dispersed throughout the layer on one side and with a nonadhesiogenic HA/CMC layer on the other side.

EXAMPLE 6

0.67 g of chopped PGA fibers (Deknatel, Inc.) were added to 400 ml of 100% ethanol. 0.64 g of fibrinogen, 22 mg of thrombin and 100 mg of calcium chloride were added to the ethanol slurry and collected on Teflon forming fabric using a Millipore filter housing (dia.=7.4). The wet sample was pressed once at 10 psi with a roll press and dried at 120–125° F. with a drum dryer. A thick paper-like membrane resulted with a M/A of 36.6 mg/cm$^2$. The hemostatic paper was very absorbent and formed a fibrin clot when immersed in water.

EXAMPLE 7

2.0 g of PGA fibers (Deknatel, Inc.) were chopped into ~5–10 mm segments and added to 600 ml of ethanol. In a separate vessel, 2.6 g of lyophilized bovine fibrinogen (77% protein, 90% clottable), 67 mg of bovine thrombin, and 0.3 g of calcium chloride powder were added to 900 ml of 100% ethanol and high shear blended with an Ultra-Turrax T50 with a G45G dispersing head for 30 seconds at 5000 rpm. The materials were combined and collected on Teflon forming fabric in a 4.25×4.25 inch headbox. The material drained in approximately 10 seconds without vacuum assistance. The fibrous cake was pressed once at 10 psi with a roll press and dried at 125–135° F. for ~30 minutes. An 11.3 cm×11.4 cm soft paper resulted with a M/A of 31.8 mg/cm$^2$.

EXAMPLE 8

410 ml of HA/CMC pulp (1.8 g of HA/CMC in 100% ethanol) was diluted with 590 ml of 100% ethanol, and 2.6 g of lyophilized bovine fibrinogen (77% protein, 90% clottable), 67 mg of bovine thrombin and 0.3 g of calcium chloride were added and high shear blended with an Ultra-Turrax T50 with a G45G dispersing head for 15 seconds at 5000 rpm. The mixture was then collected on Teflon forming fabric in a 4.25×4.25 inch headbox. The material was drained for 60 seconds without vacuum assistance and for 135 seconds with vacuum assistance. The resulting fibrous cake was pressed once at 10 psi with a roll press and dried at 125–135° F. for ~30 minutes. An 11.2×12.8 cm paper resulted with a M/A of 31 mg/cm.

EXAMPLE 9

Samples of materials produced according to Examples 4 and 8 were tested in a platelet aggregation assay as described by Wagner et al., *J. Surg. Res.* 66:100–108 (1996) using Coulter Counter Model J.T. (Coutler, Corp.). Both of these materials reduced platelet count by 45% compared to 9.5%, 13% and 23% with Gelfoam®) (absorbable gelatin sponge, Upjohn) Avitene® (microfibrillar collagen hemostat, Davol), and Actifoam™ (absorbable collagen hemostatic sponge, MedChem Products), respectively.

EXAMPLE 10

A sample prepared according to the method described in Example 8 was evaluated for sealing/hemostatic properties in the rabbit vena cava model. The vena cava of 26 anesthetized, heparinized (150 IU/kg), 4–5 kg New Zealand White rabbits was each punctured using a 16 gauge needle. A 1 cm$^2$ piece of the sample from Example 8, Avitene®, TachoComb® or surgical gauze was applied for 20 seconds directly over the puncture with light finger pressure. The pressure was removed after 20 seconds and the breakthrough bleeding was observed. In the case of no further bleeding, observation was continued for 10 min. to ensure hemostasis. In the case of breakthrough bleeding, another 1 cm$^2$ piece was applied over the first piece for another 20 seconds with light finger pressure. In the case of continued bleeding, the applications continued until a total of 10 minutes had elapsed. The results of this study are set forth in Table 1.

TABLE 1

Hemostasis/Sealant Model

| Group | Average No. Applications | Average Time to Hemostasis |
|---|---|---|
| Control Gauze (n = 9) | 15.4 ± 2.1* | 8/9 > 600 seconds† |
| Avetene ® (n = 6) | 1.5 ± 0.2 | 49.0 ± 16.4 seconds |
| TachoComb ® (n = 5) | 6.0 ± 3.7* | >361 ± seconds† |
| HA/CMC/Fib/Thromb/Ca paper (n = 6) | 1.0 ± 0.2 | 25.8 ± seconds |

*Statistically significant from HA/CMC/Fib/Thromb/Ca paper (Anova p = 0.001, Tukey-Kramer)

†Statistically significant from HA/CMC/Fib/Thromb/Ca paper (Anova p = 0.0005, Tukey-Kramer)

The results of this study demonstrate the statistically superior hemostatic activity of the HA/CMC/Fibrinogen/Thrombin paper produced according to the methods of the invention as compared to Avitene® and TachoComb® in heparinized animals. The time to hemostasis was reduced by 48% compared to Avitene® and 14 times compared to TachoComb®. The results further demonstrate that the composition of the invention also required fewer applications than either Avitene® or TachoComb®.

EXAMPLE 11

The preparation described in Example 8 was evaluated for resealing properties in the rabbit vena cava puncture model described in Example 10. The test article was initially placed over the wound, and hemostasis was achieved within approximately 20 seconds. The wound was monitored for a further 10 minutes to ensure that complete hemostasis had occurred. The test composition was then removed from the vena cava in one piece using forceps, and bleeding reinitiated. The previously used test composition was then replaced onto the wound and hemostasis was again achieved within approximately 20 seconds.

TachoComb® (collagen sponge coated with thin layers of fibrinogen and thrombin, Nycomed, Austria) and Avitene® were also tested for repositioning and resealing qualities in this model. TachoComb® could not be removed in one piece, and the collagen layer separated from the fibrinogen and thrombin layer. Avitene® could not be removed in one piece or repositioned on the wound.

The results of this study demonstrate that compositions of the invention have improved physico-mechanical properties over both TachoComb® and Avitene® . Therefore, the compositions of the invention can be removed and repositioned during use without a decrease in hemostatic or sealing capabilities, a significant advantage over the prior art hemostatic compositions.

EXAMPLE 12

The preparation described in Example 8 was also tested for the ability to function in the presence of excess amounts of blood in the rabbit vena cava puncture model. The vena cava was punctured with a 16 gauge needle, and blood was allowed to fill the abdominal cavity. A 1 $cm^2$ piece of the hemostatic composition of Example 8 was blindly applied to the wound for 20 seconds with finger pressure, and the excess blood was removed. Hemostasis was achieved in one application within 20 seconds. In contrast, Avitene® fell apart when inserted into the blood-filled abdominal cavity.

EXAMPLE 13

The hemostatic composition prepared in Example 8 was sterilized by gamma irradiation (2.5 MRad) and evaluated in the rabbit vena cava puncture model. Hemostasis was achieved in all three animals tested with one application for 20 seconds.

EXAMPLE 14

1.8 g of PGA fibers (Deknatel, Inc.) were chopped into 5–10 mm segments and added to 400 ml of 100% ethanol. In a separate vessel, 2.5 g of lyophilized bovine fibrinogen (77% protein, 90% clottable), 67 mg of bovine thrombin, 0.3 g of calcium chloride and 140 ml of HA/CMC pulp (0.6 g of HA/CMC in 100% ethanol) were added to 1000 ml of 100% ethanol and high shear blended with an Ultra-Turrax T50 with a G45G dispersing head for 15 seconds at 5000 rpm. The materials were combined, stirred, and collected on Teflon forming fabric (150 gm) in a 4.24×4.25 inch headbox. The material was drained for 60 seconds without vacuum assistance. The resulting fibrous cake was pressed once at 10 psi with a roll press and dried at 125–135° F. for ~15 minutes. An 11.4×11.4 cm soft paper resulted with a M/A of 35 $mg/cm^2$.

EXAMPLE 15

67 mg of bovine thrombin and 0.3 g of calcium chloride were added to 450 ml of 100% ethanol and high shear blended with an Ultra-Turrax T50 with a G45G dispersing head for 15 seconds at 4000 rpm. 2.5 g of lyophilized bovine fibrinogen (77% protein, 90% clottable) was added to the mixture and high shear blended with an Ultra-Turrax T50 with a G45G dispersing head for 15 seconds at 4000 rpm. 1.8 g of PGA fibers (Deknatel) were chopped into ~10 mm segments, added to 350 ml of 100% ethanol, and then added to the fibrinogen/thrombin/calcium chloride mixture.

140 ml of HA/CMC pulp (0.6 g of HA/CMC in 100% ethanol) was diluted with 860 ml of 100% ethanol and collected on Teflon forming fabric (150 gm) in a 4.24×4.25 inch headbox. The material was drained until the remaining ethanol level was ~1 inch above the settled HA/CMC material (~150 seconds).

The PGA/fibrinogen/thrombin/calcium chloride mixture was then slowly added over the HA/CMC material. The material was allowed to drain for 60 seconds with vacuum assistance. Two different layers could be differentiated in the resulting fibrous cake. The cake was pressed once at 10 psi with a roll press and dried at 125–132° F. for ~20 minutes. An 11.2 cm×11.2 cm bilayer paper resulted with a M/A of 31 $mg/cm^{2,}$ and the HA/CMC layer for adhesion prevention and the PGA/fibrinogen/thrombin/calcium chloride layer for hemostasis could be distinguished visually.

EXAMPLE 16

Samples of materials produced according to Example 6 were tested in a platelet aggregation assay as described by Wagner et al., supra, using Multisizer Model 0217 (Coulter, Corp.). These materials reduced the volume in the platelet region (2–4.5 $\mu$m) by 27% compared to 0% with TachoComb® (Nycomed), Gelfoam® (Upjohn) and Novacol® (Datascope), By 11% with Avitene® (Davol), and by 19% with Actifoam™ (MedChem).

EXAMPLE 17

1.8 g of PGA fibers (Deknatel) were chopped into ~5–10 mm segments and added to 300 ml of 100% ethanol. In a separate vessel, 121 mg (3630 U) of bovine thrombin and 0.3 g of calcium chloride were added to 700 ml of 100% ethanol and high shear blended with an Ultra-Turrax T50 with a G45G dispersing head for 15 seconds at 5000 rpm. Seventy milliliters of HA/CMC pulp (0.3 g of HA/CMC in 100% ethanol) was added during the last 5 seconds of mixing. The materials were combined, stirred, and collected on Teflon forming fabric (150 $\mu$m) in a 4.25×4.25 inch headbox. The material drained in 20 seconds without vacuum assistance. The fibrous cake was pressed once at 10 psi with a roll press and dried at 125–145° F. for ~10 min. An 11.2×11.2 cm soft paper resulted with a M/A of 17.9 $mg/cm^2$.

EXAMPLE 18

Samples produced according to Examples 7, 8 and 14 were evaluated for dry and wet mechanical properties and compared to Avitene® and TachoComb®. A 10 mm×50 mm piece of each material was placed in the grips of Instron Model 4201. The initial gauge length was 25 mm. Each material was tested under dry conditions at the crosshead speed of 2 mm/min. To test wet strength, materials were placed in 30 ml of PBS, pH 7.2 at 37° C. for 15 minutes and measurements were taken at 23° C. at a crosshead speed of 5 mm/min. immediately after removal from the PBS. Maximum load before the material breaks is indicative of the strength of the material. The results of this study (Table II) demonstrate that the hemostatic materials of the invention have statistically significant increased dry and wet strength over both Avitene® and TachoComb®.

TABLE II

Mechanical Properties of Hemostats

| Sample Type | Dry Testing Max. Load | Wet Testing Max. Load |
| --- | --- | --- |
| PGA/F/T/Ca (Ex. 7) | 0.34 ± 0.04# | 0.5645 ± 0.0782 |
| HA/CMC/F/Ca (Ex. 8) | 9.11 ± 0.92 ^ | 1.8275 ± 0.977 ^ |

TABLE II-continued

Mechanical Properties of Hemostats

| Sample Type | Dry Testing Max. Load | Wet Testing Max. Load |
|---|---|---|
| PGA/HA:CMC/F/T/Ca (Ex. 14) | 6.86 ± 0.57 ^ | 1.2738 ± 0.2308 ^ |
| TachoComb ® | 1.83 ± 0.18 | 0.5242 ± 0.1099 |
| Avitene ® | 0.12 ± 0.08 | nd* |

*Sample fell apart and could not be tested
^ Difference from TachoComb ® and Avitene ® (Anova p = 0.01, Tukey-Kramer)
Difference from Avitene ® (Anova p = 0.02, Tukey-Kramer)

Other Embodiments

From the above description, one skilled in the art can easily ascertain the essential characteristics of the present invention, and without departing from the spirit and scope thereof, can make various changes and modifications of the invention to adapt it to various uses and conditions. For example, components including but not limited to plasticizers, polyethylene glycol, glycerol, and albumin can also be included in the composition of the invention to provide additional stability, mechanical strength and flexibility.

We claim:

1. A solid, bioabsorbable hemostatic composition comprising a bioabsorbable polymer and a hemostatic compound, wherein the hemostatic compound is dispersed throughout the hemostatic composition, said hemostatic compound prepared by combining, in a non-aqueous solvent, thrombin, fibrinogen and a calcium salt, wherein said fibrinogen is not activated by thrombin during processing.

2. The composition of claim 1 wherein the bioabsorbable polymer is selected from the group consisting of polyanionic polysaccharides, chitin, chitosan, polyglycolide, polylactide, polycaprolactone, and copolymers thereof.

3. The composition of claim 1 wherein the bioabsorbable polymer is a polyanionic polysaccharide.

4. The composition of claim 3 wherein the polyanionic polysaccharide is in the form of a water-insoluble derivative.

5. The composition of claims 3 or 4 wherein the polyanionic polysaccharide is selected from the group consisting of carboxymethylcellulose, carboxymethylamylose, and hyaluronic acid.

6. The composition of claims 3 or 4 wherein the hemostatic composition comprises two or more polyanionic polysaccharides.

7. The composition of claim 3 or 4 further comprising a hydrophobic bioabsorbable polymer.

8. The composition of claim 7 wherein the hydrophobic bioabsorbable polymer is selected from the group consisting of polyglycolide, polylactide, polydioxanones, polyestercarbonates, polyhydroxyalkonates, polylactones and copolymers thereof.

9. The composition of claim 1 wherein the thrombin is present at a concentration between about 1 and 100 U/cm$^2$.

10. The composition of claim 1 wherein the fibrinogen is present in a concentration between about 0.05 and 20 mg/cm$^2$.

11. The composition of claim 1 wherein the calcium salt is calcium chloride.

12. The composition of claim 1 wherein the calcium salt is present in a concentration between 0.01 and 10 mg/cm$^2$.

13. The composition of claim 11 wherein the fibrinogen is present in a concentration between about 0.05 and 20 mg/cm$^2$.

14. The composition of claim 1 further comprising Factor XIII, fibronectin, plasminogen, aprotinin, alpha-2-antiplasmin, alpha-2-macroglobulin, alpha-1-antitrypsin, epsilon-aminocaproic acid, tranexamic acid, a plasmin activator inhibitor, or a combination thereof.

15. The composition of claim 1 further comprising protamine sulfate.

16. The composition of claim 1 further comprising a drug.

17. The composition of claim 16 wherein the drug is selected from the group consisting of growth factors, growth factor inhibitors, antibodies, non-steroidal anti-inflammatory agents, antibiotics and cytokines.

18. The composition of claim 1 having a mass/area between about 15 and 50 mg/cm$^2$.

19. The composition of claim 1 wherein the composition is provided in a waterproof, sterile package.

20. The composition of claim 1 further comprising a medically acceptable adhesive backing.

21. The composition of claim 1 wherein the composition is formed to fit over the ends of a vascular prosthesis.

22. A kit comprising the hemostatic composition of claim 1.

23. The composition of claim 1 wherein the hemostatic compound is dispersed evenly throughout the composition.

24. The composition of claim 1 wherein the hemostatic compound is present as a gradient.

25. The composition of claim 1 further comprising a bilayer composition with one layer containing the hemostatic compound and the other layer containing the bioabsorbable polymer.

26. A method of making a solid, bioabsorbable hemostatic composition comprising the steps of a) admixing a bioabsorbable polymer and a hemostatic compound in a non-aqueous solvent to form a fibrous pulp, said hemostatic compound comprising thrombin, fibrinogen and a calcium salt, wherein the thrombin does not activate the fibrinogen during processing; and b) subjecting the fibrous pulp to a paper-making process to form a paper product.

27. The method of claim 26 wherein the non-aqueous solvent is selected from the group consisting of straight-chain or branched C1–C5 alcohols, ketones, aliphatic ethers, cycloaliphatic ethers, esters, nitrites, and aliphatic halogenated hydrocarbons.

28. The method of claim 27 wherein the non-aqueous solvent is an alcohol.

29. The method of claim 28 wherein the alcohol is ethanol.

30. The method of claim 28 wherein the alcohol is 95% to 100% ethanol.

31. The method of claim 26 wherein the bioabsorbable polymer and hemostatic compound are admixed under high shear conditions.

32. The method of claim 26 wherein the paper-making process includes the steps a) collecting the fibrous pulp from the non-aqueous solvent;

b) pressing the collected fibrous pulp; and c) drying the pressed pulp.

33. The method of claim 32 wherein the fibrous pulp is collected onto a forming fabric.

34. The method of claim 33 wherein the forming fabric is selected from the group consisting of Teflon mesh, stainless steel mesh and polyester fabric.

35. The method of claim 33 wherein the forming fabric is a polyester fabric.

36. The method of claim 32 wherein the collected fibrous pulp is subjected to heat compression.

37. A method for inhibiting or stopping blood loss from a wound comprising contacting the wound with a solid, biodegradeable hemostatic composition comprising a bioabsorbable polymer and a hemostatic compound for a period of time sufficient to promote blood clotting to occur, said hemostatic compound being prepared by combining, in a non-aqueous solvent, thrombin, fibrinogen and a calcium salt, wherein said fibrinogen is not activated by thrombin during processing.

38. The method of claim 37 further comprising applying manual pressure hemostatic composition after contact with the wound.

39. The method of claim 37 wherein the wound is caused by accidental trauma.

40. The method of claim 37 wherein the wound is due to a surgical procedure.

41. A solid, bioabsorbable hemostatic composition prepared according to the method of claim 26.

42. A solid, bioabsorbable hemostatic composition prepared according to the method of claim 32.

* * * * *